(12) United States Patent
Richter et al.

(10) Patent No.: US 10,464,948 B2
(45) Date of Patent: Nov. 5, 2019

(54) POLYCYCLIC DIIMINOOXADIAZINONES

(71) Applicant: Covestro Deutschland AG, Leverkusen (DE)

(72) Inventors: Frank Richter, Leverkusen (DE); Patrizio Orecchia, Berlin (DE); Max Widemann, Haiterbach-Beihingen (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 15/989,288

(22) Filed: May 25, 2018

(65) Prior Publication Data

US 2018/0346482 A1    Dec. 6, 2018

(30) Foreign Application Priority Data

May 30, 2017  (EP) ..................................... 17173345
Jun. 9, 2017   (LU) ................................... LU100278

(51) Int. Cl.
*C07D 498/14* (2006.01)
*C08G 18/79* (2006.01)

(52) U.S. Cl.
CPC ........... *C07D 498/14* (2013.01); *C08G 18/79* (2013.01)

(58) Field of Classification Search
CPC .................................................. C07D 498/14
See application file for complete search history.

(56) References Cited

U.S. PATENT DOCUMENTS

| | | | |
|---|---|---|---|
| 2,853,473 | A | 9/1958 | Campbell et al. |
| 5,516,935 | A | 5/1996 | Bischof et al. |
| 5,717,091 | A | 2/1998 | Richter et al. |
| 5,882,544 | A | 3/1999 | Richter et al. |
| 6,020,066 | A | 2/2000 | Weisser et al. |
| 2002/0045723 | A1 | 4/2002 | Richter et al. |
| 2007/0043152 | A1 | 2/2007 | Bernard et al. |

OTHER PUBLICATIONS

H.J. Laas et al., Journal für Praktische Chemie, The Synthesis of Aliphatic Polyisocyanates Containing Biuret, Isocyanurate or Uretdione Backbones for Use in Coatings, 1994, 336, 185-200.

*Primary Examiner* — Laura L Stockton
(74) *Attorney, Agent, or Firm* — John E. Mrozinski, Jr.

(57) ABSTRACT

The invention relates to polycyclic diiminooxadiazinones of the formula I and/or of the formula II,

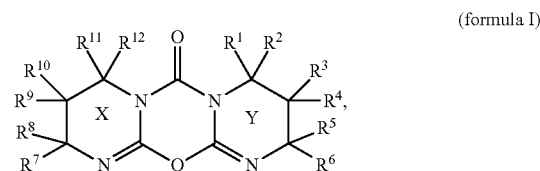
(formula I)

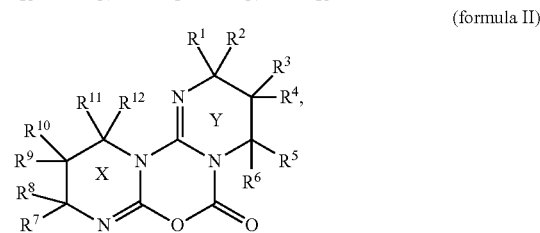

(formula II)

in which in each case
$R^1$ to $R^{12}$ are each independently hydrogen, a saturated or unsaturated, linear or branched, aliphatic or cycloaliphatic organic radical having 1 to 20 carbon atoms, which is unsubstituted or is substituted by radicals inert to isocyanate groups, and/or comprises heteroatoms inert to isocyanate groups in the chain, or are an aromatic organic radical having 6 to 20 carbon atoms, which is unsubstituted or is substituted by radicals inert to isocyanate groups,
wherein two or more of the aforementioned radicals $R^1$ to $R^6$ may form further rings, in each case with one another and incorporating one, two or three carbon atoms of the fused ring segment X, and/or two or more of the aforementioned radicals $R^7$ to $R^{12}$ may form further rings, in each case with one another and incorporating one, two or three carbon atoms of the fused ring segment Y.

17 Claims, No Drawings

POLYCYCLIC DIIMINOOXADIAZINONES

CROSS REFERENCE TO RELATED APPLICATION

The present application claims priority under the Paris Convention to LU Serial No. LU100278, filed Jun. 9, 2017, and to EP Serial Number 17173345.4, filed May 30, 2017, the entire contents of each are incorporated herein by reference.

FIELD OF THE INVENTION

The invention relates to polycyclic diiminooxadiazinones, to a method for the preparation thereof and to the use of the polycyclic diiminooxadiazinones as reactive components and the reaction products obtainable from the polycyclic diiminooxadiazinones.

BACKGROUND OF THE INVENTION

The substance class of the diiminooxadiazinones A is currently entirely unknown, which—without wishing to be bound to scientific theories—might be accounted for by the significantly higher stability of the isomeric iminotriazinediones B. The latter can be formed by modifying isocyanates in varying proportions and are known, for example, from US 2007/0043152 A1.

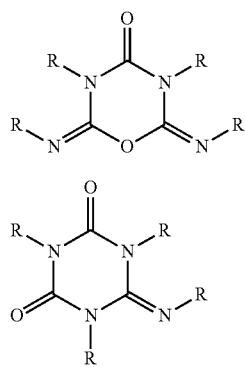

SUMMARY OF THE INVENTION

The present invention provides potential cross-linkers for polyurethane chemistry, which do not contain any free highly reactive isocyanate groups, but nevertheless are reactive to compounds comprising Zerevitinov-reactive hydrogen atoms.

It is understood that the invention disclosed and described in this specification is not limited to the embodiments summarized in this Summary.

DETAILED DESCRIPTION OF THE INVENTION

The present invention will now be described for purposes of illustration and not limitation. Except in the operating examples, or where otherwise indicated, all numbers expressing quantities, percentages, and so forth in the specification are to be understood as being modified in all instances by the term "about."

Any numerical range recited in this specification is intended to include all sub-ranges of the same numerical precision subsumed within the recited range. For example, a range of "1.0 to 10.0" is intended to include all sub-ranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited in this specification is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein. All such ranges are intended to be inherently described in this specification such that amending to expressly recite any such sub-ranges would comply with the requirements of 35 U.S.C. § 112(a), and 35 U.S.C. § 132(a). The various embodiments disclosed and described in this specification can comprise, consist of, or consist essentially of the features and characteristics as variously described herein.

Any patent, publication, or other disclosure material identified herein is incorporated by reference into this specification in its entirety unless otherwise indicated, but only to the extent that the incorporated material does not conflict with existing definitions, statements, or other disclosure material expressly set forth in this specification. As such, and to the extent necessary, the express disclosure as set forth in this specification supersedes any conflicting material incorporated by reference herein. Any material, or portion thereof, that is said to be incorporated by reference into this specification, but which conflicts with existing definitions, statements, or other disclosure material set forth herein, is only incorporated to the extent that no conflict arises between that incorporated material and the existing disclosure material. Applicant reserves the right to amend this specification to expressly recite any subject matter, or portion thereof, incorporated by reference herein.

The present invention provides polycyclic diiminooxadiazinones of the formula I and/or of the formula II,

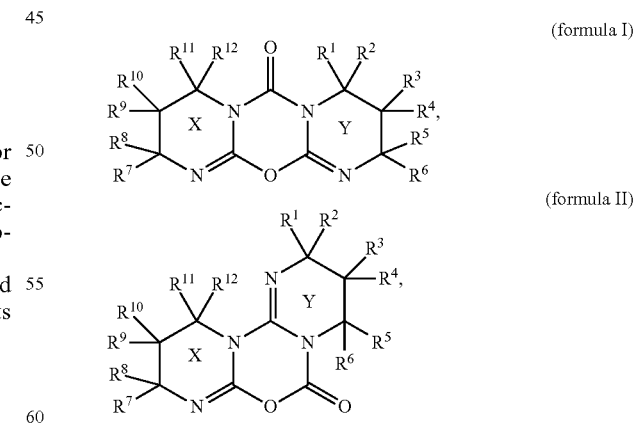

in which in each case $R^1$ to $R^{12}$ are each independently hydrogen, a saturated or unsaturated, linear or branched, aliphatic or cycloaliphatic organic radical having 1 to 20 carbon atoms, which is unsubstituted or is substituted by radicals inert to isocyanate groups, and/or comprises heteroatoms inert to isocyanate groups in the chain, or are an aromatic organic radical having 6 to 20 carbon atoms, which is unsubstituted or is wherein two or more of the aforementioned radicals $R^1$ to $R^6$ may form further rings, in each case with one another and incorporating one, two or three carbon atoms of the fused ring segment X, and/or two or more of the aforementioned radicals $R^7$ to $R^{12}$ may form further rings, in each case with one another and incorporating one, two or three carbon atoms of the fused ring segment Y.

The one, two or three carbon atoms of the fused ring segments X and Y optionally included in further rings are the available $sp^3$-hybridized carbon atoms of the fused ring segments X and Y.

The one, two or three carbon atoms of the fused ring segments X and Y optionally included in further rings are preferably those carbon atoms to which the corresponding ring-forming radical $R^1$ to $R^{12}$ is attached.

In the context of the present invention, radicals inert to isocyanate groups are understood to mean all substituents not bearing any Zerevitinoff-active hydrogen atoms.

In the context of the present invention, a "Zerevitinoff-reactive hydrogen atom" is defined as an acidic hydrogen atom or "active" hydrogen atom. A hydrogen atom of this kind is determined in a manner known per se by reactivity to an appropriate Grignard reagent. The amount of Zerevitinoff-active hydrogen atoms is typically measured by the release of methane, which occurs in accordance with the reaction equation below during a reaction of the substance to be tested R—XH (the functionality —XH bonds to the rest of the molecule R) with methylmagnesium bromide ($CH_3$—MgBr):

$$CH_3\text{—MgBr} + R\text{—XH} \rightarrow CH_4 + Mg(XR)Br$$

In the context of the present invention, heteroatoms inert to isocyanate groups in the chain are understood to mean in particular O, S and SiR', also NR', in which the substituents R' are in turn radicals inert to isocyanate groups having the definitions stated above.

Preferably, the references to "comprising", "containing", etc. mean "consisting essentially of" and most preferably "consisting of".

In a first preferred embodiment, $R^1$ to $R^{12}$ are each independently hydrogen, a saturated or unsaturated, linear or branched, aliphatic or cycloaliphatic organic radical having 1 to 10 carbon atoms, which is unsubstituted or is substituted by radicals inert to isocyanate groups, and/or comprises heteroatoms inert to isocyanate groups in the chain, or are an aromatic organic radical having 6 to 12 carbon atoms, which is unsubstituted or is substituted by radicals inert to isocyanate groups, wherein two or more of the aforementioned radicals $R^1$ to $R^6$ may form further rings, in each case with one another and incorporating one, two or three carbon atoms of the fused ring segment X, and/or two or more of the aforementioned radicals $R^7$ to $R^{12}$ may form further rings, in each case with one another and incorporating one, two or three carbon atoms of the fused ring segment Y.

It is further preferred in this context that $R^1$ to $R^{12}$ are each independently hydrogen, a saturated or unsaturated, linear or branched, aliphatic or cycloaliphatic organic radical having 1 to 6 carbon atoms, which is unsubstituted or is substituted by radicals inert to isocyanate groups, and/or comprises heteroatoms inert to isocyanate groups in the chain, wherein two or more of the aforementioned radicals $R^1$ to $R^6$ may form further rings, in each case with one another and incorporating one, two or three carbon atoms of the fused ring segment X, and/or two or more of the aforementioned radicals $R^7$ to $R^{12}$ may form further rings, in each case with one another and incorporating one, two or three carbon atoms of the fused ring segment Y.

In a further preferred embodiment, $R^1$ to $R^{12}$ are each independently hydrogen or $C_1$-$C_{10}$-alkyl(ene), preferably each independently hydrogen or $C_1$-$C_6$-alkyl(ene) and particularly preferably each independently hydrogen or $C_1$-$C_4$-alkyl(ene).

In a further preferred embodiment, the heteroatoms inert to isocyanate groups are oxygen, sulfur, tertiary nitrogen and/or quaternary silicon, wherein the substituents on the nitrogen and silicon are inert to isocyanate groups, preference being given to oxygen and/or sulfur and particular preference being given to oxygen.

In the case of the rings formed optionally from two or more of the radicals $R^1$ to $R^6$, in each case with one another and incorporating one, two or three carbon atoms of the fused ring segment X, and/or rings formed optionally from two or more of the radicals $R^7$ to $R^{12}$, in each case with one another and incorporating one, two or three carbon atoms of the fused ring segment Y, the definition of the radicals $R^1$ to $R^{12}$ specified in each case above applies, and also of the embodiments thereof specified as preferred, in which it is particularly preferred that the rings optionally formed have 5 to 8 carbon atoms in the ring, particularly preferably 5 to 6 carbon atoms in the ring, in which these rings may comprise heteroatoms selected from the group consisting of oxygen, sulfur, tertiary nitrogen and/or quaternary silicon, in which the substituents on the nitrogen and silicon are inert to isocyanate groups.

According to a further preferred embodiment of the polycyclic diiminooxadiazinones of the formula I and/or of the formula II according to the invention, the radicals $R^2$ and $R^5$ form a further ring with one another and incorporate the three $sp^3$-hybridized carbon atoms of the fused ring segment X and the radicals $R^8$ and $R^{12}$ form a further ring with one another and incorporate the three $sp^3$-hybridized carbon atoms of the fused ring segment Y.

It is furthermore preferred in this case that the polycyclic diiminooxadiazinones according to the invention comprise compounds of the formula III and/or compounds of the formula IV,

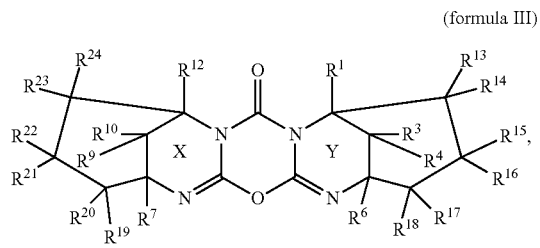

(formula III)

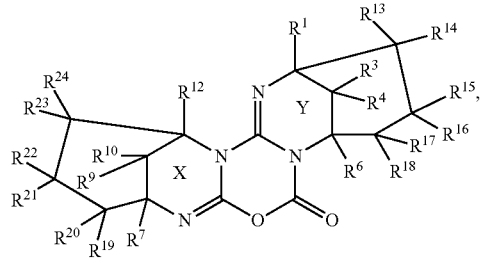

(formula IV)

in which in each case $R^1$, $R^3$, $R^4$, $R^6$, $R^7$, $R^9$, $R^{19}$ and $R^{12}$ are each independently hydrogen, a saturated or unsaturated, linear or branched, aliphatic or cycloaliphatic organic radical having 1 to 20 carbon atoms, which is unsubstituted or is substituted by radicals inert to isocyanate groups, and/or comprises heteroatoms inert to isocyanate groups in the chain, or are an aromatic organic radical having 6 to 20 carbon atoms, which is unsubstituted or is substituted by radicals inert to isocyanate groups, and $R^{13}$ to $R^{24}$ are each independently hydrogen, a saturated or unsaturated, linear or branched, aliphatic or cycloaliphatic organic radical having 1 to 20 carbon atoms, which is unsubstituted or is substituted by radicals inert to isocyanate groups, and/or comprises heteroatoms inert to isocyanate groups in the chain, or are an aromatic organic radical having 6 to 20 carbon atoms, which is unsubstituted or is substituted by radicals inert to isocyanate groups, wherein two or more of the aforementioned radicals $R^1$, $R^3$, $R^4$, $R^6$, $R^{13}$ to $R^{18}$ may form further rings in each case with one another and/or two or more of the aforementioned radicals $R^7$, $R^9$, $R^{10}$, $R^{12}$, $R^{19}$ to $R^{24}$ may form further rings in each case with one another.

The present invention further relates to a method for preparing the polycyclic diiminooxadiazinones according to the invention, in which at least two diisocyanates, in which the two NCO groups are in a 1,3-position to each other, are cyclized with elimination of $CO_2$. This cyclization is also referred to below as a reaction and may also be carried out in two stages.

In a first preferred embodiment of the method according to the invention, the at least two diisocyanates are cyclized in a first step i) to give a polycyclic iminooxadiazinedione, which a) is isolated and is converted to the polycyclic diiminooxadiazinone in a further step ii) or b) is converted without isolation directly to the polycyclic diiminooxadiazinone in a further step ii).

In a likewise preferred embodiment, simultaneous $CO_2$ elimination and cyclization to the polycyclic diiminooxadiazinones according to the invention is carried out. Suitable catalysts for this purpose are, for example, typical carbodiimidization catalysts as described in U.S. Pat. No. 2,853,473 for example.

The at least bicyclic iminooxadiazinediones are described on page 2, line 40 to page 3, line 25 of EP 0 761 670 A2.

Suitable diisocyanates in which the two NCO groups are in a 1,3-position to each other are preferably in the molecular weight range of 126 to 500 g/mol, particularly preferably of 126 to 350 g/mol. Examples of such 1,3-diisocyanates are propane 1,3-diisocyanate, butane 1,3-diisocyanate, pentane 1,3-diisocyanate, pentane 2,4-diisocyanate and other isomers of the diisocyanates specified above with the NCO groups having a 1,3-position to each other, such as 2,2-dimethylpropane 1,3-diisocyanate for example. In the case of cycloaliphatic polyisocyanates, the cyclic system linked directly in the 1,3-position to the for the formation of the polycyclic diiminooxadiazinone structure according to the invention generally comprises 4 to 8, preferably 5 or 6, particularly preferably 6 carbon atoms and may comprise any inert substituents, especially alkyl groups, preferably those having 1 to 4 carbon atoms. Particular preference is given to those 1,3-diisocyanatocyclohexanes comprising one or more $C_1$-$C_{20}$-alkyl substituents in the 2- and/or in the 4-position. Suitable 1,3-diisocyanatocycloalkanes are, for example, 1,3-diisocyanatocyclopentane, 1,3-diisocyanatocyclohexane, 1,3-diisocyanatocyclooctane, 1,3-diisocyanato-2-methylcyclohexane, 1,3-diisocyanato-4-methylcyclohexane and any technical grade mixtures of the two latter diisocyanates, 1,3-diisocyanato-2-isopropylcyclohexane, 1,3-diisocyanato-4-isopropylcyclohexane, 1,3-diisocyanato-2,4-dimethylcyclohexane, 1,3-diisocyanato-2,4-diethylcyclohexane, 1,3-diisocyanato-2,4-diethyl-6-methylcyclohexane, 1,3-diisocyanato-2-methyl-4,6-diethylcyclohexane and any technical grade mixtures of the two latter diisocyanates or 1,3-diisocyanato-2,4,6-triisopropylcyclohexane and 1,3-diisocyanato-2,4,6-tributylcyclohexane.

It is irrelevant by which methods the aforementioned isocyanates are generated, i.e. with or without use of phosgene. In this case, however, the phosgenation of the corresponding amines in the gas phase is particularly preferred, since in this manner the result is purer products in higher yields than in the case of phosgenation in the liquid phase (cf. EP 0 676 392 A1 and EP 0 764 633 A1). Alternatively, the aforementioned diisocyanates are also accessible by phosgene-free textbook methods, such as the Curtius rearrangement of appropriately substituted carbonyl azides for example, wherein the latter do not have to be isolated without solvent but rather are accessible in situ, for example from carboxylic acids and carboxylic acid derivatives and azides of a wide variety of structures.

The reaction of the aforementioned 1,3-diisocyanates to give the polycyclic diiminooxadiazinones according to the invention may be carried out without solvent or in dilution with solvents inert to isocyanates. In a further preferred embodiment of the method according to the invention, the reaction is carried out in the presence of at least one solvent. This is preferred in order to suppress the extent of intermolecular reactions forming high molecular weight isocyanate conversion products, i.e. of compounds composed of more than 2 monomer units. If carried out with dilution, the use of solvents which boil above 150° C. at the applied pressure is preferred but not a requirement.

These reactions are typically conducted with catalysis, in which a whole series of isocyanate-active compounds may be used as catalysts, which are generally used for so-called isocyanate modification and are described, for example, in H. J. Laas et al., *J. Prakt. Chem.* 1994, 336, 185 ff. The oligo- or polymerization of isocyanates, especially forming high molecular weight oligomer mixtures having uretdione ("dimer"), isocyanurate ("trimer") and/or iminooxadiazinedione structures ("asymmetric trimer") in the molecular skeleton, is referred to here as isocyanate modification, which are explicitly not target compounds in the present document, but whose partial formation in addition to the inventive polycyclic diiminooxadiazinones is quite tolerable for many customary fields of application of the inventive polycyclic diiminooxadiazinones.

It was very surprising and unexpected to those skilled in the art that, in the reaction according to the invention of specific diisocyanates in which the two NCO groups are arranged in a 1,3-position to each other, these generally known, high molecular weight, modified polyisocyanates are (mainly) not formed, but rather the isocyanate group-free inventive polycyclic diiminooxadiazinones which are discrete molecules of a currently completely unknown structural type.

In a further preferred embodiment of the method according to the invention, the cyclization is effected in the presence of at least one catalyst.

It is further preferred in this case that the catalyst is a phosphane or a phosphane oxide, preference being given to a compound comprising at least one phosphorus atom in a 5-membered ring and particular preference being given to a phospholane oxide or a phospholene oxide.

If the method is carried out according to the abovementioned preferred embodiment comprising steps i) and ii), the catalyst is present at least in step i).

The catalysts used for the reaction according to the invention are preferably organophosphorus compounds such as phosphanes and phosphane oxides. The reaction may also be conducted in this case such that the tertiary phosphanes that are very suitable for the formation of the at least bicyclic iminooxadiazinediones from the 1,3-diisocyanates on which they are based are oxidized to the corresponding P-oxides after substantially complete formation of the former and thus catalyze the subsequent formation of the inventive polycyclic diiminooxadiazinones having at least one additional fused ring compared to the at least bicyclic iminooxadiazinediones.

Examples include (from "propyl" on all isomers): triethylphosphane, tripropylphosphanes, tributylphosphanes, tripentylphosphanes, trihexylphosphanes, cyclopentyldimethylphosphane, cyclopentyldiethylphosphane, cyclopentyldipropylphosphanes, cyclopentyldibutylphosphanes, cyclopentyldihexylphosphanes, cyclopentyldioctylphosphanes, dicyclopentylmethylphosphane, dicyclopentylethylphosphane, dicyclopentyl-n-propylphosphanes, dicyclopentylbutylphosphanes, dicyclopentylhexylphosphanes, dicyclopentyloctylphosphanes, tricyclopentylphosphane, cyclohexyldimethylphosphane, cyclohexyldiethylphosphane, cyclohexyldipropylphosphanes, cyclohexyldibutylphosphanes, cyclohexyldihexylphosphanes, cyclohexyldioctylphosphanes, dicyclohexylmethylphosphane, dicyclohexylethylphosphane, dicyclohexylpropylphosphanes, dicyclohexylbutylphosphanes, dicyclohexylhexylphosphanes, dicyclohexyloctylphosphanes, tricyclohexylphosphane and the P-oxides of the aforementioned compounds.

Furthermore, compounds may also be used as catalysts in which the phosphorus atom is part of an n-membered ring, which for its part may also optionally comprise $sp^2$-hybridized carbon atoms, where n is a natural number which is preferably 5 or 6. In particular, the P-oxides of these five-membered ring species are already known from U.S. Pat. No. 2,853,473 as excellent carbodiimidization catalysts. Examples include: 1-methyl-1-phospholane oxide, 1-methyl-1-phosphol-2-ene oxide, 1-methyl-1-phosphol-3-ene oxide, 1,3-dimethyl-1-phosphol-2-ene oxide, 1,3-dimethyl-1-phosphol-3-ene oxide, 1,3,4-trimethyl-1-phosphol-2-ene oxide, 1,3,4-trimethyl-1-phosphol-3-ene oxide, 1-ethyl-1-phospholane oxide, 1-ethyl-1-phosphol-2-ene oxide, 1-ethyl-1-phosphol-3-ene oxide, 1-ethyl-3-methyl-1-phosphol-2-ene oxide, 1-ethyl-3-methyl-1-phosphol-3-ene oxide, 1-ethyl-3,4-dimethyl-1-phosphol-2-ene oxide, 1-ethyl-3,4-dimethyl-1-phosphol-3-ene oxide, 1-phenyl-1-phospholane oxide, 1-phenyl-1-phosphol-2-ene oxide, 1-phenyl-1-phosphol-3-ene oxide, 1-phenyl-3-methyl-1-phosphol-2-ene oxide, 1-phenyl-3-methyl-1-phosphol-3-ene oxide, 1-phenyl-3,4-dimethyl-1-phosphol-2-ene oxide, 1-phenyl-3,4-dimethyl-1-phosphol-3-ene oxide.

In particular, the phosphanes are also good catalysts for the formation of the at least bicyclic iminooxadiazinediones from the 1,3-diisocyanates on which they are based. These at least bicyclic iminooxadiazinediones may be regarded as precursors of the polycyclic diiminooxadiazinones according to the invention. For instance, it is possible to decarboxylate the former to the latter also by purely thermal means in the absence of catalysts. Therefore, one embodiment of the method according to the invention is also preferred in which the reaction in step ii) is thermally induced.

The reaction may be terminated after any selected degree of conversion of the monomeric compound(s), for example by adding a catalyst poison, by thermal deactivation of the catalyst or by simple cooling of the reaction mixture. In the latter case, it should preferably be ensured when selecting the catalyst that the catalyst no longer has sufficient (residual) activity when passing through the critical temperature range for nylon-1 formation or that this temperature range is passed through sufficiently rapidly (quench) such that fractions of unreacted monomers potentially present do not react, or only react to a tolerable extent for the application of the respective product, to give cyclopolymeric nylon-1. Such problems are not to be expected if the reaction is conducted up to the point of essentially complete consumption of the 1,3-diisocyanates. Otherwise, remaining unreacted monomers may subsequently be removed by a method from the prior art, such as distillation, thin-film distillation or extraction for example.

The polycyclic diiminooxadiazinones according to the invention may be isolated, optionally in a mixture with other isocyanate conversion products, by the customary methods from the prior art such as, for example, thin-film distillation, extraction, crystallization or molecular distillation and are obtained in this case as colourless or slightly coloured liquids or solids. The latter, depending on the isocyanate or the isocyanate mixture(s) used, have a melting point range of ca. 30-250° C.

The polycyclic diiminooxadiazinones according to the invention are exceptionally valuable raw materials which are suitable both as an intermediate for producing or formulating active ingredients and for use in the plastics and coatings sector.

In the latter application field, they can be used in pure form or in combination with other isocyanate derivatives from the prior art, such as polyisocyanates containing uretdione, biuret, allophanate, isocyanurate, urethane and carbodiimide groups whose free NCO groups optionally have been deactivated with typical blocking agents.

The present invention therefore further relates to the use of the polycyclic diiminooxadiazinones according to the invention as a component or intermediate for producing polyurethane plastics, foamed polyurethane plastics, lacquers and coating compositions.

In the present case, the definition of "polyurethane" also includes the structurally analogous polyureas, which can be prepared by reacting NCO groups with polyamines known to those skilled in the art, wherein the "polyurethanes" in the narrower sense can be prepared by reacting NCO groups with polyhydroxy compounds.

The particular advantage of the polycyclic diiminooxadiazinones according to the invention is on the one hand considered to be that they do not have any tendency to split back into the monomeric diisocyanates on which they are based even in the case of prolonged thermal stress, but on the other hand have sufficiently high reactivity towards many compounds comprising Zerevitinov-active hydrogen.

The present invention further relates to a composition comprising at least one polycyclic diiminooxadiazinone according to the invention and at least one compound comprising one or more Zerevitinov-active hydrogen atoms.

The resulting plastics and coatings correspond in their chemical nature largely to those which are obtained based on (coating) raw materials of (cyclo)aliphatic diisocyanates comprising biuret and allophanate groups and are thus exceptionally high value products with the typical property profile for the proven systems of the prior art mentioned but without having the disadvantages already addressed.

The present invention also relates to a composite, obtainable or obtained by reacting at least one composition according to the invention, which in the case where the composite is a coating, has previously been applied to a substrate.

In addition to the method products according to the invention and the further binder components and lacquer solvents or lacquer solvent mixtures optionally used therewith, such as toluene, xylene, cyclohexane, chlorobenzene, butyl acetate, ethyl acetate, ethylglycol acetate, methoxypropyl acetate, acetone, white spirit, more highly substituted aromatics (SOLVENTNAPHTHA, SOLVESSO, SHELLSOL, ISOPAR, NAPPAR, DIASOL), further auxiliaries and additives may also be used in the coatings such as, for example, wetting agents, flow control agents, anti-skinning agents, antifoam agents, matting agents, viscosity-regulating substances, pigments, dyes, UV absorbers and stabilizers against thermal and oxidative influences.

The coating agent based on the polycyclic diiminooxadiazinones according to the invention may be used for coating numerous materials such as, for example, wood, plastic, leather, metal, paper, concrete, masonry, ceramics and textiles.

The present invention further relates to the use of the polycyclic diiminooxadiazinones according to the invention as an intermediate for producing or formulating active ingredients and/or pharmaceutical products.

The present invention likewise relates to the polycyclic diiminooxadiazinones according to the invention for use as medicaments.

The examples and comparative examples which follow are intended to further illustrate the invention but without limiting it thereto.

EXAMPLES

All percentages and ppm data, unless noted otherwise, are based on weight.

All reactions were carried out under a nitrogen atmosphere.

Mol % figures were determined by NMR spectroscopy and always relate, unless specified otherwise, to the sum total of the NCO conversion products. The measurements were effected on the BRUCKER DRX 700 instrument on ca. 1% ($^1$H NMR) or ca. 50% ($^{13}$C NMR) samples in dry $C_6D_6$ at a measurement frequency of 700 MHz ($^1$H NMR) or 176 MHz ($^{13}$C NMR). The $C_6D_5H$ present in the solvent was used as reference signal for the ppm scale: $^1$H NMR chemical shift 7.15 ppm, $^{13}$C NMR chemical shift 128.02 ppm.

The diisocyanates used are products of Covestro Deutschland AG, D-51365 Leverkusen; all other commercially available chemicals were sourced from Aldrich, D-82018 Taufkirchen. 1-Methyl-2-phospholene 1-oxide and 1-methyl-3-phospholene 1-oxide, CAS-No. 872-45-7 and 930-38-1 (approximately equimolar isomeric mixture, MPO in the text below) are products of Clariant AG, Muttenz, CH.

Example 1 Thermal Cyclization of at Least Bicyclic Iminooxadiazinediones

By reacting an in each case 10% solution of
a) 1,3-diisocyanatopropane
b) 1,3-diisocyanato-3-methylbutane or
c) 1,3-diisocyanatocyclohexane (cis/trans isomeric mixture)
in o-dichlorobenzene at 120° C. with ca. 10 mol % (based on the respective diisocyanate) tri-n-butylphosphane, the respective bicyclic iminooxadiazinediones were obtained, which were purified by vacuum distillation/sublimation and characterized by NMR and GC-MS.

In b) mainly one isomer was surprisingly formed with high selectivity (others were detected at very low concentration in the crude reaction mixture by GC-MS), which could be assigned, by X-ray crystallographic investigations, the structure having a tertiary linked free NCO group and two methyl groups on the adjacent carbon atom localized to the imino function. In c) only the cis-isomer reacted; the trans isomer was separated by distillation with the excess o-dichlorobenzene as forerun.

The products thus obtained were heated to 220° C. for 5 h and analyzed after cooling.

The identity of the simplest derivative of the compound class according to the invention, obtained from Example 1a), where $R^1$ to $R^{12}$=H in formula I, was identified unequivocally by NMR and X-ray crystallographic investigations after sublimation under vacuum and recrystallization. The presence of the isomer of the structure II (at significantly lower concentration than I) in the crude reaction mixture was confirmed by NMR and GC-MS.

Also in Examples 1b and 1c, the isomers of the general formula I were predominantly formed and were obtained in pure form by means of vacuum sublimation and subsequent recrystallization. In the crude reaction mixtures, however, the isomers of the structure II (at significantly lower concentration than I) were likewise detected by NMR and GC-MS.

Example 2 Catalytic Formation from the Monomeric Diisocyanates

By reacting an in each case 10% solution of
a) 1,3-diisocyanatopropane
b) 1,3-diisocyanato-3-methylbutane or
c) 1,3-diisocyanatocyclohexane (cis/trans isomeric mixture)
in o-dichlorobenzene at 180° C. with ca. 5 mol % (based on the respective diisocyanate) MPO, the respective polycyclic diiminooxadiazinones were obtained, which were purified by vacuum distillation/sublimation and characterized by NMR and GC-MS. The products thus obtained did not differ from those which were isolated according to Example 1. The total yield (based on the primary 1,3-diisocyanate used) was however significantly higher than in Example 1.

Example 3 Reaction with Zerevitinoff-Active H Containing Substrates

The tricyclic diiminooxadiazinone obtained from 1,3-diisocyanatopropane as described in Example 2a) was dissolved in excess 1-butanol and 1-nonane thiol, respectively, and stirred for 3-4 hrs at 100° C. Complete conversion was observed in both cases, indicated by the complete disappearance of the signals (in a 2:1 intensity ratio) at 140.7 and 146.4 in the 13C NMR spectrum. Instead, three new downfield signals appeared at 155.2, 153.9 and 149.6 ppm (reaction with 1-butanol) and 155.7, 153.0 and 151.9 ppm (reaction with 1-nonane thiol), respectively, indicative for the formation of O-alkylisourea and S-alkylisothiourea, respectively.

This model reaction confirms that the tricyclic diiminooxadiazinones according to the invention are suitable as NCO-free crosslinkers in polyurethane chemistry. In analogy to the examples described di- or poly(thi)ols would furnish high molecular weight products.

This specification has been written with reference to various non-limiting and non-exhaustive embodiments. However, it will be recognized by persons having ordinary skill in the art that various substitutions, modifications, or combinations of any of the disclosed embodiments (or portions thereof) may be made within the scope of this specification. Thus, it is contemplated and understood that this specification supports additional embodiments not expressly set forth herein. Such embodiments may be obtained, for example, by combining, modifying, or reorganizing any of the disclosed steps, components, elements, features, aspects, characteristics, limitations, and the like, of the various non-limiting embodiments described in this specification. In this manner, Applicant reserves the right to amend the claims during prosecution to add features as variously described in this specification, and such amendments comply with the requirements of 35 U.S.C. § 112(a), and 35 U.S.C. § 132(a).

The invention claimed is:

1. A polycyclic diiminooxadiazinone of the formula I or of the formula II,

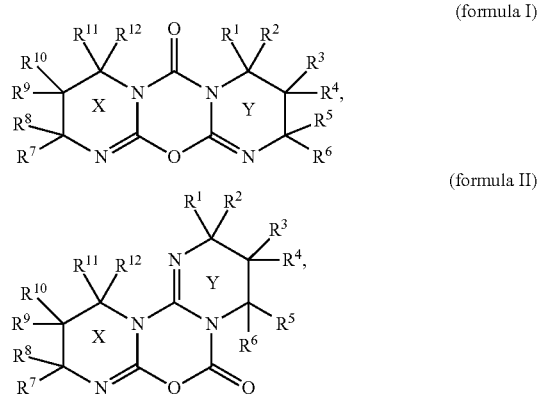

(formula I)

(formula II)

in which in each case
$R^1$ to $R^{12}$ are each independently hydrogen, a saturated or unsaturated, linear or branched, aliphatic or cycloaliphatic organic radical having 1 to 20 carbon atoms, which is unsubstituted or is substituted by radicals inert to isocyanate groups, and/or comprises heteroatoms inert to isocyanate groups in the chain, or are an aromatic organic radical having 6 to 20 carbon atoms, which is unsubstituted or is substituted by radicals inert to isocyanate groups,
wherein two or more of the aforementioned radicals $R^1$ to $R^6$ may form further rings, in each case with one another and incorporating one, two or three carbon atoms of the fused ring segment X, and/or two or more of the aforementioned radicals $R^7$ to $R^{12}$ may form further rings, in each case with one another and incorporating one, two or three carbon atoms of the fused ring segment Y.

2. The polycyclic diiminooxadiazinone according to claim 1, wherein
$R^1$ to $R^{12}$ are each independently hydrogen, a saturated or unsaturated, linear or branched, aliphatic or cycloaliphatic organic radical having 1 to 10 carbon atoms, which is unsubstituted or is substituted by radicals inert to isocyanate groups, and/or comprises heteroatoms inert to isocyanate groups in the chain, or are an aromatic organic radical having 6 to 12 carbon atoms, which is unsubstituted or is substituted by radicals inert to isocyanate groups,
wherein two or more of the aforementioned radicals $R^1$ to $R^6$ may form further rings, in each case with one another and incorporating one, two or three carbon atoms of the fused ring segment X, and/or two or more of the aforementioned radicals $R^7$ to $R^{12}$ may form further rings, in each case with one another and incorporating one, two or three carbon atoms of the fused ring segment Y.

3. The polycyclic diiminooxadiazinone according to claim 1, wherein $R^1$ to $R^{12}$ are each independently hydrogen or $C_1$-$C_{10}$-alkyl(ene).

4. The polycyclic diiminooxadiazinone according to claim 1, wherein the heteroatoms inert to isocyanate groups are oxygen, sulfur, tertiary nitrogen and/or quaternary silicon, wherein the substituents on the nitrogen and silicon are inert to isocyanate groups.

5. A polycyclic diiminooxadiazinone of the formula III or of the formula IV,

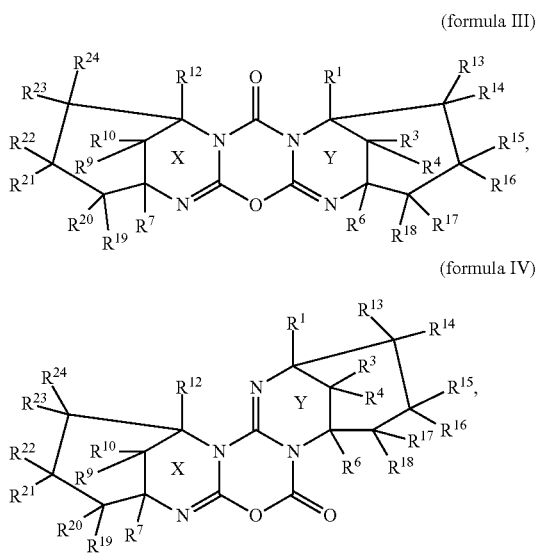

(formula III)

(formula IV)

in which in each case
$R^1$, $R^3$, $R^4$, $R^6$, $R^7$, $R^9$, $R^{10}$ and $R^{12}$ are each independently hydrogen, a saturated or unsaturated, linear or branched, aliphatic or cycloaliphatic organic radical having 1 to 20 carbon atoms, which is unsubstituted or is substituted by radicals inert to isocyanate groups, and/or comprises heteroatoms inert to isocyanate groups in the chain, or are an aromatic organic radical having 6 to 20 carbon atoms, which is unsubstituted or is substituted by radicals inert to isocyanate groups, and
$R^{13}$ to $R^{24}$ are each independently hydrogen, a saturated or unsaturated, linear or branched, aliphatic or cycloaliphatic organic radical having 1 to 20 carbon atoms, which is unsubstituted or is substituted by radicals inert to isocyanate groups, and/or comprises heteroatoms inert to isocyanate groups in the chain, or are an aromatic organic radical having 6 to 20 carbon atoms, which is unsubstituted or is substituted by radicals inert to isocyanate groups, wherein two or more of the aforementioned radicals $R^1$, $R^3$, $R^4$, $R^6$, $R^{13}$ to $R^{18}$ may form further rings in each case with one another and/or two or more of the aforementioned radicals $R^7$, $R^9$, $R^{10}$, $R^{12}$, $R^{19}$ to $R^{24}$ may form further rings in each case with one another.

6. A method for preparing a polycyclic diiminooxadiazinone according to claim 1, wherein at least two diisocyanates, in which the two NCO groups are in a 1,3-position to each other, are cyclized with elimination of $CO_2$.

7. The method according to claim 6, wherein the diisocyanates are cyclized in a first step i) to give a polycyclic iminooxadiazinedione, which
   a) is isolated and is converted to the polycyclic diiminooxadiazinone in a further step ii) or
   b) is further converted without isolation directly to the polycyclic diiminooxadiazinone in a further step ii).

8. The method according to claim 6, wherein the cyclization is effected in the presence of at least one catalyst.

9. The method according to claim 8, wherein the catalyst is a phosphane or a phosphane oxide.

10. The method according to claim 7, wherein the reaction in step ii) is thermally induced.

11. The method according to claim 6, wherein the reaction is carried out in the presence of at least one solvent.

12. A composition comprising at least one polycyclic diiminooxadiazinone according to claim 1 and at least one compound comprising one or more Zerevitinoff-active hydrogen atoms.

13. A medicament comprising the polycyclic diiminooxadiazinone according to claim 1.

14. The polycyclic diiminooxadiazinone according to claim 1, wherein $R^1$ to $R^{12}$ are each independently hydrogen or $C_1$-$C_6$-alkyl(ene).

15. The polycyclic diiminooxadiazinone according to claim 1, wherein $R^1$ to $R^{12}$ are each independently hydrogen or $C_1$-$C_4$-alkyl(ene).

16. The method according to claim 8, wherein the catalyst is a compound comprising at least one phosphorus atom in a 5-membered ring.

17. The method according to claim 8, wherein the catalyst is a pholane oxide or a phospholene oxide.

* * * * *